United States Patent [19]

Hung et al.

[11] Patent Number: 5,298,033
[45] Date of Patent: Mar. 29, 1994

[54] ULTRAVIOLET ABSORBING LENSES AND METHODS OF MANUFACTURING THEREOF

[75] Inventors: William M. Hung; Kai C. Su, both of Alpharetta, Ga.

[73] Assignee: Ciba-Geigy Corporation, Ardsley, N.Y.

[21] Appl. No.: 3,674

[22] Filed: Jan. 12, 1993

Related U.S. Application Data

[63] Continuation of Ser. No. 707,515, May 30, 1991, abandoned, which is a continuation-in-part of Ser. No. 468,386, Jan. 22, 1990, Pat. No. 5,098,445, which is a continuation-in-part of Ser. No. 323,354, Mar. 14, 1989, Pat. No. 4,929,250, and Ser. No. 323,327, Mar. 14, 1989, Pat. No. 4,963,160.

[51] Int. Cl.$^5$ .............................. D06P 3/52; D06P 5/20
[52] U.S. Cl. .............................................. 8/509; 8/444; 8/507; 8/543; 8/544; 8/549; 8/648; 544/224
[58] Field of Search ................... 8/507, 648, 509, 544, 8/549

[56] References Cited

U.S. PATENT DOCUMENTS

| | | | |
|---|---|---|---|
| Re. 27,401 | 6/1972 | Wichterle et al. | 521/142 |
| 2,976,576 | 3/1961 | Wichterle et al. | 264/49 |
| 3,041,330 | 6/1962 | Coleman et al. | 536/31 |
| 3,055,896 | 9/1962 | Boyle et al. | 8/120 |
| 3,159,646 | 12/1964 | Milionis et al. | 548/261 |
| 3,213,058 | 10/1965 | Boyle et al. | 528/96 |
| 3,214,436 | 10/1965 | Boyle et al. | 548/260 |
| 3,399,173 | 8/1965 | Heller et al. | 526/259 |
| 3,493,539 | 2/1970 | Skoultchi et al. | 526/259 |
| 3,629,191 | 12/1971 | Heller et al. | 524/91 |
| 3,766,285 | 10/1973 | Heller et al. | 585/8 |
| 3,862,087 | 1/1975 | Heller et al. | 528/186 |
| 4,257,692 | 3/1981 | Le Naour-Sene | 8/471 |
| 4,286,957 | 9/1981 | Le Naour-Sene | 8/471 |
| 4,390,676 | 6/1983 | Loshaek | 526/313 |
| 4,418,000 | 11/1983 | Zannucci et al. | 252/403 |
| 4,418,001 | 11/1983 | Zannucci et al. | 252/403 |
| 4,418,002 | 11/1983 | Zannucci et al. | 252/403 |
| 4,528,311 | 7/1985 | Beard et al. | 524/91 |
| 4,559,059 | 12/1985 | Su | 8/507 |
| 4,785,063 | 11/1988 | Slongo et al. | 526/259 |
| 4,826,978 | 5/1989 | Migdal | 544/216 |
| 4,880,859 | 11/1989 | Slongo et al. | 524/91 |
| 4,892,915 | 1/1990 | Slongo et al. | 526/259 |
| 4,929,250 | 5/1990 | Hung et al. | 8/507 |
| 4,954,132 | 9/1990 | Hung et al. | 8/507 |
| 4,963,160 | 10/1990 | Hung et al. | 8/507 |
| 4,981,487 | 1/1991 | da Costa | 8/507 |
| 5,098,445 | 3/1992 | Hung et al. | 8/507 |

FOREIGN PATENT DOCUMENTS 981539 1/1965 United Kingdom.

Primary Examiner—A. Lionel Clingman
Attorney, Agent, or Firm—Edward McC. Roberts; William G. Hervey

[57] ABSTRACT

An ultraviolet radiation absorbing agent for bonding to an ocular lens. The agent has the formula $$A-NH-B$$

wherein A is an ultraviolet absorbing compound and B is a specific reactive group or a moiety containing reactive group.

2 Claims, No Drawings

ULTRAVIOLET ABSORBING LENSES AND METHODS OF MANUFACTURING THEREOF

The present invention is a continuation of application Ser. No. 07/707,515 filed May 30, 1991, now abandoned, which is a continuation-in-part of Ser. No. 07/468,386 filed Jan. 22, 1990, now U.S. Pat. No. 5,098,445 which was a continuation-in-part of Ser. Nos. 323,354, now U.S. Pat. No. 4,929,250, and 323,327, now U.S. Pat. No. 4,963,160, both filed Mar. 14, 1989.

BACKGROUND OF THE INVENTION

The present invention relates to ultraviolet radiation absorbing contact lenses and to a method for their preparation. More particularly, the invention relates to hydrophilic or "soft" contact lenses having a reactive ultraviolet radiation absorbing agent covalently bonded to polymeric material.

Ultraviolet radiation is ever present in our environment, and consists of wave lengths between 200-380 nm. Exposure to ultraviolet radiation has been found to be the cause of several ocular pathologies. The damaging effect of ultraviolet radiation on the corneal epithelium has been known for a long time. For instance, studies have demonstrated the damaging effect of 290 nm radiation on the rabbit corneal epithelium (Cullen, A. P. (1980): *Ultraviolet Induced Lysosome Activity in Corneal Epithelium*, Graefes Arch Clin Exp. Ophthalmol 214:107-118), as well as changes in the stroma and endothelium of primary corneal layers (epithelium, stroma and endothelium) subsequent to exposure to a commercially available UV suntan lamp which emits radiation across the full spectrum from 280 nm (Ringvold, A., et al. (1985): *Changes in the Rabbit Corneal Stroma Caused by UV-Radiation*, Acta Ophthalmol. (Copenh) 63:601-606). Compounding the damage is the fact that ultraviolet radiation damage to the eye is known to be cumulative and obeys the law of reciprocity. These findings reinforce the importance of adequate ocular protection against ultraviolet radiation. Such protection is particularly recommended for people who are prone to UV exposure, patients who have had cataract surgery and patients on photo-sensitizing drugs.

Recently, contact lenses have been developed which serve to absorb ultraviolet radiation. For example, U.S. Pat. No. 4,390,676 discloses an ultraviolet absorbing contact lens formed by copolymerizing a monomer suitable for making lenses and an ultraviolet absorber for absorbing radiation having wavelengths of 340 to 450 nm. The UV absorbing compound, 2-hydroxy-4-methacryloxy-benzophenone or mixtures thereof, is incorporated into the lens' polymeric material at the molecular level. Also, U.S. Pat. No. 4,528,311 discloses ultraviolet light absorbing contact lenses made of a polymeric composition comprising copolymers of 2-hydroxy-5-acrylyloxyphenyl-2H-benzotriazole with one or more other monomers copolymerizable therewith.

The above compounds have been found to copolymerize and give protection to the material. However, the copolymerization efficiency of the compounds has proved to be inadequate. Typically, no more than 15% of the alkenyloxy-benzophenones actually become part of the polymeric chain. The remainder of the material is easily leached out by solvent extraction. Furthermore, while the hydroxy benzophenones copolymerizable with acrylate monomers are effective UV absorbers and form chemically stable copolymers, relatively large amounts, i.e. 3 to 10% by weight, must be incorporated in the polymer to obtain 85% UV absorption at 400 nm and 1 mm thickness. Also, the compounds exhibit very broad absorption bands which extend into the visible spectrum, and lenses incorporating these ingredients tend to be unacceptably yellow in color.

The above described UV absorbing lenses also possess several limitations. For instance, the absorbing agents and the lens material have different properties, and only one absorbing agent is used and appears symmetrically as a thick film on the lens. As a result, the lenses have structural weaknesses and exhibit inconsistent expansion, which in turn results in overly curved or otherwise misshapened lenses. Furthermore, the application of the agent to the lens takes a relatively long time, must be done at high temperature, and requires a high concentration of the expensive agent.

There exists, therefore, a need for improved ultraviolet radiation absorbing contact lenses, as well as a method for their production.

There also exists a need for such lenses which have structural integrity, which can be prepared in relatively short time and at relatively low temperatures and which use small amounts of UV absorbing agents.

There exists a further need for such lenses which absorb a broad range of UV wavelengths.

There exists a more particular need for a lens which incorporates a relatively small amount of absorbing agent, which exhibits relatively little yellowing, and from which the absorbing agent does not leach out.

SUMMARY OF THE INVENTION

The present invention relates to ultraviolet radiation absorbing lenses, and a method for their production, comprising a UV absorbing agent covalently bonded to a polymeric lens material. The lens exhibits very little yellowing, and can be produced using a relatively small amount of the absorbing agent. Also, because of the covalent bonding, the absorbing agent does not leach from the lens.

The absorbing agent has the formula:

A—NH—B wherein A is an ultraviolet radiation absorbing component and
wherein B is a reactive group of a moiety containing reactive group selected from the group consisting of

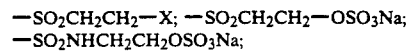

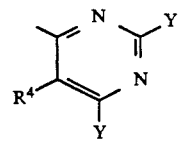

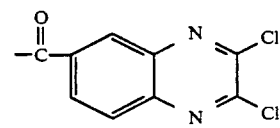

-continued

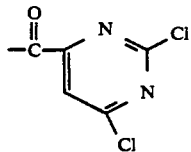

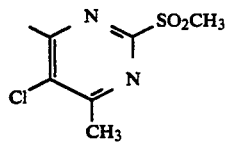

or 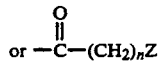

wherein
X = a halogen;
R⁴ = H or Cl;
Y = Cl or F;
n = 1 or 2 and
Z = a halogen,

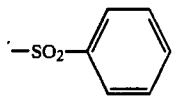

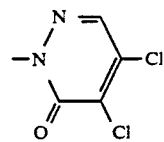

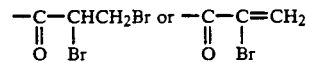

The agent should be water soluble (at least in the tinting conditions of use) because the step of incorporating the agent onto the lens material is performed in an aqueous medium.

It has also been found that the absorbing agent of the present invention can be applied to a lens at about 50° C. and in a relatively short time by simply dipping or otherwise placing the lens into a aqueous medium having the agent dissolved therein. This enables the agent to be applied to the lens by an optometrist at the point of purchase, rather than at the facility where the lens is made. Therefore, the optometrist does not need to maintain a large inventory of already absorbent lenses.

DETAILED DESCRIPTION OF THE INVENTION

While the present invention is applicable to introcular lenses and lenses used in spectacles, it will be described in connection with contact lenses. The present invention relates to lenses having UV absorbing agent bonded to its polymeric lens material. The absorbing agent is water soluble and is bound to the polymeric lens material exoskelatally.

The present invention employs a reactive ultraviolet absorbing agent of the following formula:

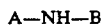 A—NH—B wherein A is an ultraviolet radiation absorbing component and whereing B is a reactive group or a moiety containing reactive group selected from the group consisting of

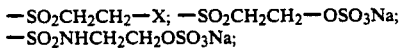

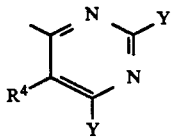

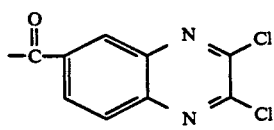

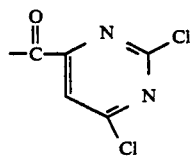

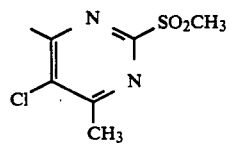

or 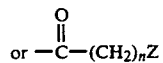

where
X = a halogen;
R⁴ = H or Cl;
Y = Cl or F;
n = 1 or 2 and
Z = a halogen,

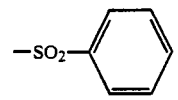

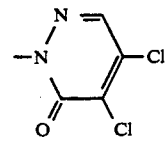

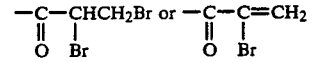

Typical radicals of UV absorbers are those radicals of UV absorbers disclosed in the following patents, all of which are incorporated herein by reference.

| U.S. Pat. No. | 3,041,330 |
| --- | --- |
| | 3,159,646 |
| | 3,213,058 |
| | 3,214,436 |
| | 4,418,000 |

-continued

|  |  |
|---|---|
|  | 4,418,001 |
|  | 4,418,002 |
|  | 4,826,978 |
|  | 3,493,539 |
|  | 3,399,173 |
|  | 4,880,859 |
|  | 4,785,063 |
| German | 1,495,870 |
| British | 981,539 |
| European | 133,164 |

UV absorbers of interest to the invention include: benzoic acid esters, cyano and carbomethoxy acrylates, oxalic acid diamides, and hydroxyphenyltriazines.

Particularly suitable for use in the instant invention as UV absorber groups are the radicals of the benzophenones and benzotriazoles. Also of particular interest are the radicals of p-(benzoic or salicylic) acids. More specifically, the UV-absorbers of interest include, without limitation, Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylamino-propyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o-and p-ethoxy-disubstituted oxanilides.

2-(2-Hydroxyphenyl)-1,3,5-triazines, for example 2,4,6-tris(2-hydroxy-4-octyloxyphenyl)-1, 3,5-triazine, 2-(2-hyroxy-4-octyloxy-phenyl)-4,6-bis(2,4-dimethyl-phenyl)-1,3, 5-triazine,2-(2,4-dihydroxy-phenyl)-4,6-bis(2,4-dimethylphenyl)-1,3, 5-triazine,2,4-bis(2-hydroxy-4-propyloxyphenyl)-6-((2,4-dimethylphenyl)-1,3,5-triazine, 2-(2-hydroxy-4-octyloxyphenyl)-4,6-bis(4-methylphenyl)-1,3, 5-triazine,2-(2-hydroxy-4-dodecyloxyphenyl)-4, 6-bis(2,4-dimethylphenyl)-1,3,5-triazine.

2-(2'-Hydroxyphenyl)benzotriazoles, for example the 5'-methyl, 3',5'-di-tert-butyl, 5'-(1,1,3,3-tetramethylbutyl), 5-chloro-3', 5'-di-tert-butyl, 5-chloro-3'-tert-butyl-5'-methyl, 3'-sec-butyl-5'-tert-butyl, 4'-octoxy, 3', 5'-di-tert-amyl and 3', 5'-bis(a,a-dimethylbenzyl) derivatives.

2-Hydroxybenzophenones, for example the 4-hydroxy, 4-methoxy, 4-octoxy, 4-decyloxy, 4-dodecyloxy, 4-benzyloxy, 4,2', 4'-trihydroxy and 2'-hydroxy-4,4'-dimethoxy derivatives.

Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)-resorcinol, benzoylresorcinol, 2,4-di-tert-butylphenyl 3', 5-di-tert-butyl-4-hydroxybenzoate and hexadecyl 3', 5-di-tert-butyl-4-hydroxybenzoate.

Acrylates, for example ethyl a-cyano-B,B-diphenylacrylate, isooctyl a-cyano-B,B-diphenylacrylate, methyl a-carbomethoxycinnamate, methyl a-cyano-B-methyl-p-methoxy-cinnamate, butyl a-cyano-B-methyl-p-methoxy-cinnamate, methyl a-carbomethoxy-p-methoxycinnamate and N-(B-carbomethoxy-B-cyanovinyl)-2-methylindoline.

The ultraviolet radiation absorbing agent A is preferably selected from the group including:

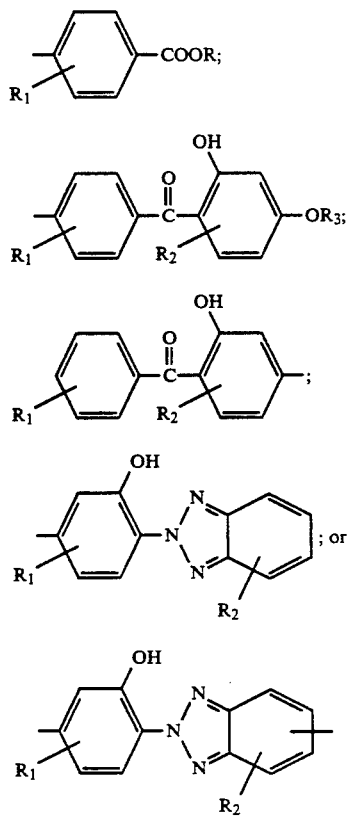

where R=H, alkyl or metal salt and
$R_1$–$R_3$=H, alkyl $C_1$ to $C_8$, $C_1$ to $C_8$ alkoxy halogen, nitrogen or sulfonate.

The compounds of the polymeric lens material may vary so long as there is present in the monomer mixture a component which will provide the polymer with the required exoskeletal functional groups. The required exoskeletal functional groups include any group that is replaced by an ultraviolet radiation absorber contain a leaving group or added to an ultraviolet radiation absorber contain an activated c=c bond. Such groups, prior to reacting include, but are limited to: hydroxy, amino, amido, mercapto, carboxy, etc.

Monomers having the above groups which are suitable for use in the invention include without limitation: hydroxyalkyl esters of polymerizable unsaturated acids, such as acrylic, methacrylic, fumaric, maleic, etc; unsaturated acids per se, such as acrylic, methacrylic, fumaric, maleic, etc; heterocyclic N-vinyl lactams, such as N-vinyl pyrrolidone, etc; noncyclic amides such as N-(1,1-dimethyl-3-oxobutyl)-acrylamide; amino alkyl esters of unsaturated acids such as 2-aminoethylacrylate, methacrylate, fumarate, or maleate; mercapto alkyl esters of unsaturated acids such as 2-mercapto ethyl acrylate, methacrylate, fumarate or maleate.

Other suitable monomers and reactive groups suitable for reacting with the reactive UV absorber will be apparent for those of ordinary skill.

In addition to the monomers having the required exoskeletal functional groups, the lens material may have a number of other monomeric components which do not have the stated reactive groups or such groups serve other purposes as when such a monomer is utilized as a crosslinking agents. The monomer, once crosslinking has taken place, is generally not available for interaction with the reactive UV absorber. However, if more than two suitable reactive groups are present, such a monomer may indeed provide suitable reactive sites for covalently bonding to the reactive UV absorber. Typical crosslinking agents may include, without limitation, ethyleneglycol dimethacrylate, diethyleneglycol bis allyl carbonate, or the like.

A highly suitable and preferable lens material is hydroxyethylmethacrylate (HEMA) as disclosed in U.S. Pat. Nos. 2,976,576 and Re. 27,401. Two acceptable "hard" lens materials are cellulose acetate butyrate and polymethylmethacrylate (PMMA).

The UV-absorber compounds of the invention may be used to make contact lenses absorb UV radiation by bonding them to the lens polymer material in the same way as the reactive dyes are used to tint contact lenses. For example, a practitioner may place a preformed contact lens in a UV absorber solution. In a standard procedure, a contact lens is rinsed with deionized water and placed in a dry vial. Base solution (typically 10% $Na_3PO_4.12H_2O$ (aq) solution) is added to the vial, followed by the UV absorber solution. The vial is shaken in a shaker bath, and the lens removed. The lens is rinsed with deionized water and extracted with 10% glycerine (aq) solution at 80° C. for two hours. The lens is once again rinsed with water, then stored in saline. This process is further improved if a quaternary ammonium salt is preferably provided in the UV absorber solution prior to placement of the lens material therein.

A number of ammonium quaternary salts may be used in practicing the improved process, including $$[A]_w[B]_z[C]_t[E]_v N^+ Q^-$$ (I)

where
each of w,z,t and v is 0-4 and $w+z+t+v=4$.
Q is a counterion selected for $HSO_4^-$, $F^-$, $Cl^-$, $Br^-$, $I^-$, $CH_3COO^-$, $OH^-$, $BF_4^-$,

$PF_6^-$, and $H_2PO_4^-$.

A, B, C, and E are each selected from $C_{1-18}$ alkyl preferably $C_{1-7}$ alkyl, more preferably $C_{1-4}$ alkyl, phenyl or phenyl-$C_{1-4}$ alkyl, in which the phenyl ring is unsubstituted or substituted by $C_1$-$C_8$ alkyl, $C_1$-$C_8$ alkoxy, halo, hydroxy, phenoxy, nitro, carboxy, acetamido, phenyl, or benzyl, cycloalkyl having 5-6 ring members, for example, tri-$C_{1-4}$ alkylbenzylammonium2 chloride, triethylbenzyl-ammonium chloride, tetraC$_{1-4}$ alkylammonium hydrogen sulfate, especially tetrabutylammonium hydrogen sulfate, phenyltriC$_{1-4}$ alkylammonium chloride, especially phenyl trimethylammonium chloride, benzyltriC$_{1-4}$ alkylammonium chloride, especially benzyltributylammonium chloride, tetraC$_{1-4}$ alkylammonium bromide, especially tetra butyl ammonium chloride or bromide, and tetraethylammonium chloride or bromide.

The following examples illustrate, but do not limit the instant invention.

The standard process for incorporating the reactive ultraviolet absorbing agent into the lens involves contacting the agent to the lens material, preferably under mild reaction conditions. In one method, for example, the lens is rinsed with deionized water and placed in a dry vial. Two milimeters each of a solution containing a reactive UV absorbing agent and diluted sodium phosphate solution are then added to the vial. The vial containing the solutions and the lens is placed in a vial rack in a shaker bath at a set temperature and speed. After a set predetermined period of time has elapsed, the lens is removed from the vial, rinsed with deionized water, and extracted with a 10% glycerine (aq) solution at 80° C. for two hours. The lens is then rinsed with water and stored in a 0.9% saline solution for 30 minutes. The transmission and/or absorbance spectrum of the lens can then be determined using a UV spectrophotometer.

A typical process for applying the absorbing agent to the lens is now set forth. A mixture of 2 ml of 0.05 to 5.0% (aq) stock solution of ultraviolet radiation absorbing agent, 2 ml of 5 to 10% (aq) $Na_3PO_4.12H_2O$, and 0.2 ml of 1 to 10% (aq) solution of tetrabutylammonium bromide was prepared. A clear lens comprised of hydroxyethyl methacrylate (HEMA) was then soaked in the mixture and heated at 50° C. for 60 minutes with agitation. The lens was then neutralized with a buffered saline solution (pH=7.0), after which the lens was extracted with 10% glycerine in an extraction bath until there was no UV absorbing agent leaching out. This was determined by a UV spectrophotometer. After the extraction process, the lens was boiled in distilled water, and then buffered with saline to remove any remaining glycerine.

The following examples illustrate the invention:

EXAMPLE I

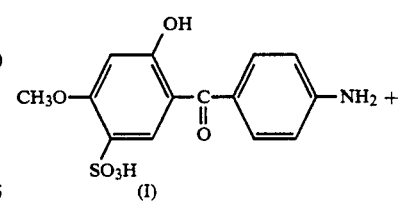

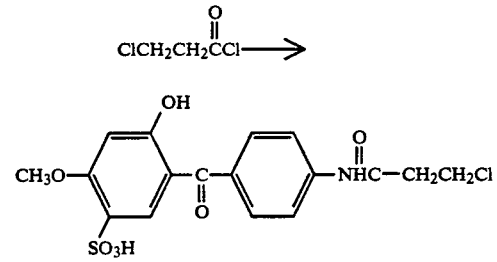

9 g of (I) was suspended in 400 ml of ethylacetate at room temperature. 15 ml of 3-chloropropionyl chloride was added dropwise to the suspension and the resulting mixture was refluxed for 30 minutes until a tarry mixture resulted. The tarry mixture was triturated with acetone and allowed to cool, and the solvent was decanted. The resultant 4'-(3-chloropropionamido)-2-hydroxy-4-methoxy-benzophenone-5-sulfonic acid reacted well with lense material and was found to be a good ultraviolet absorber.

EXAMPLE II

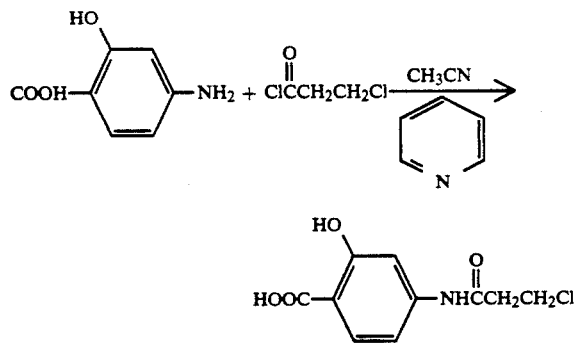

7.5 g of 4-Aminosalicyclic acid was dissolved in 300 ml of acetonitrile at about 60° C. 12 ml of 3-chloropropionyl chloride was added dropwise and followed by addition of 5 ml of pyridine, the resulting mixture was refluxed for three hours. The mixture, which became clear after approximately 20 minutes of refluxing, was cooled and evaporated to dryness under reduced pressure. A gummy oil was dissolved in isopropanol-water and refrigerated for several days. A small amount of solid thus produced was filtered off. The filtrate was evaporated to dryness and approximately 16.8 g of crude 4-(3-chloropropionamido) salicyclic acid was produced. A lens treated with this compound was found to be clear with excellent UV blockage up to about 320 nm.

EXAMPLE III

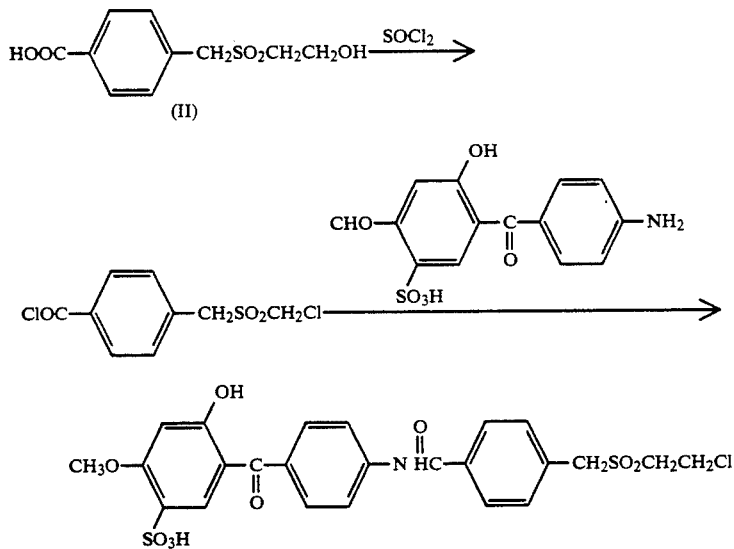

10 g of (II) was added to 100 ml of thionyl chloride at room temperature to produce a slurry. The slurry was heated at reflux for 1.5 hours and a clear solution resulted. Excess SOCl₂ was distilled off under reduced pressure. 50 ml tolVene and 50 ml of THF were added and the solution was redistilled to approximately 15 ml to drive out all the SOCl₂. A clear oil was obtained and then dissolved in 100 ml of THF.

At room temperature, the above THF solution was added to a mixture containing 12.5 g of 4'-amino-2-hydroxy-4-methoxybenzophenone-5-sulfonic acid, 0.5 g of tetrabutylammonium bromide, 15 ml of 10% sodium hydroxide, 250 ml of THF and 250 ml of water. After addition, the pH of the solution was brought to 6.5 with further addition of 10% sodium hydroxide. The mixture was then heated at 40° C. for one and half hours, cooled to room temperature and quenched the reaction mixture into 1500 ml of water. After addition of 50 g of magnesium chloride with stirring, the UV absorbing agent, 4'-[4''-(2-chloroethylsulfonylmethylphenyl) amido]-2-hydroxy-4-methoxy benzophenone-5-sulfonic acid, magnesium salt, was obtained. A lens treated with this compound was found to be clear with excellent UV blockage up to about 360 nm.

EXAMPLE IV

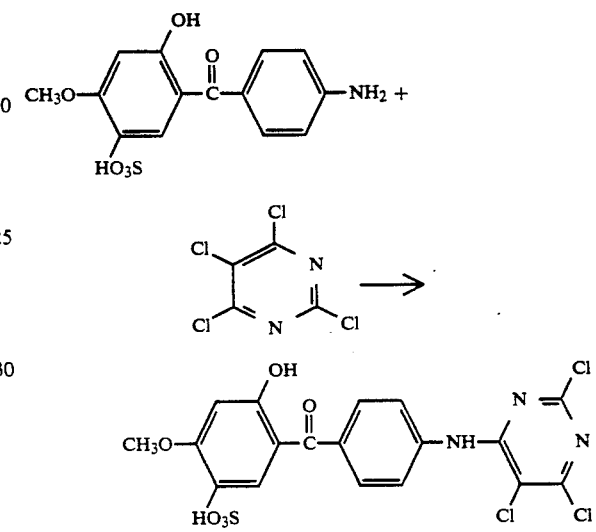

10% NaoH was added to a slurry of 5 g of 4'-amino-2-hydroxy-4-methoxy-benzophenone-5-sulfonic acid in 100 ml of water to bring the pH up to 7.4. A clear solution was resulted. To this solution was added 3.75 g of 2.4.5.6-tetrachloropyrimidine and the resulting mixture was heated at 45° C. for 3 hours. The pH was maintained at 7.0–7.5 by addition of dilute sodium hydroxide.

The mixture was cooled and 3.1 g of 4'-[6-(2,4,5-trichloropyriamidinyl)]-amino-2-hydroxy-4-methoxy-benzophenone-5-sulfonic acid was collected. The above compound reacted well with lens material and effectively absorbed UV wavelength up to 360 nm.

EXAMPLE V

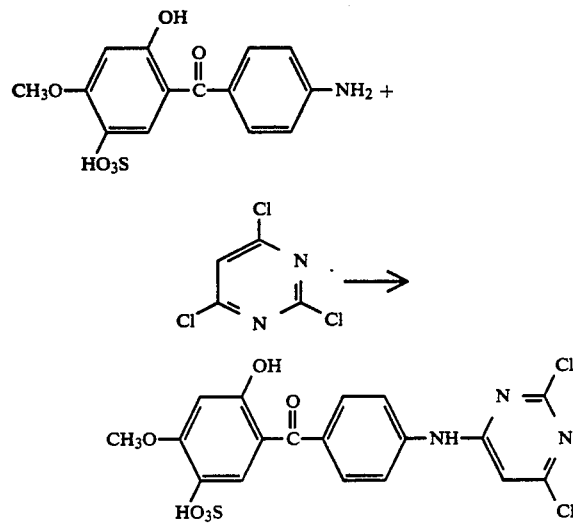

Proceeding in a matter similar to that described in example IV above, 10.0 g of 4'-amino-2-hydroxy-4-methoxy-benzophenone-5-sulfonic acid and 6.0 g of 2.4.6-trichloropyrimidine were interacted in water-acetone mixture to obtain 1.7 g of 4'-[6-(2,4-dichloropyrimidinyl)]-amino-2-hydroxy-4-methoxy-benzophenone-5-sulfonic acid. The compound reacted well with lens material and effectively absorbed UV wavelength up to 375 nm.

EXAMPLE VI

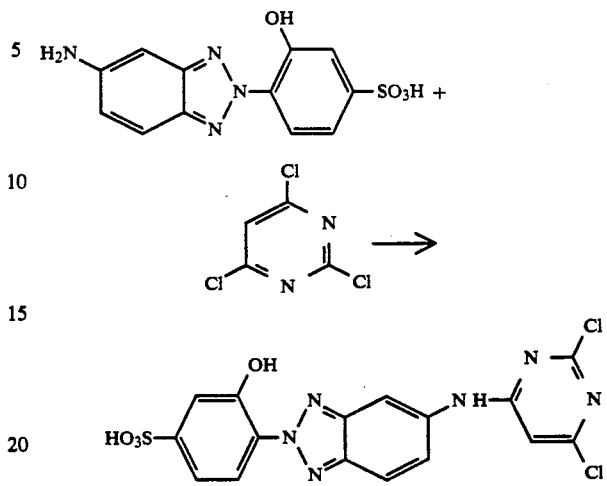

Following the procedure described in Example V above except replacing 4'-amino-2-hydroxy-4-methoxybenzophenone-5-sulfonic acid with 4-(5'-aminobenzotriazol-2-yl)-3-hydroxybenzene sulfonic acid, there was obtained dark colored 4-[5-[6-(2,4 dichloropyrimidinyl)]aminobenzotriazol-2yl]-3-hydroxybenzenesulfonic acid. A lens treated with this compound was wine-red in color and possessed excellent UV blockage.

EXAMPLE VII

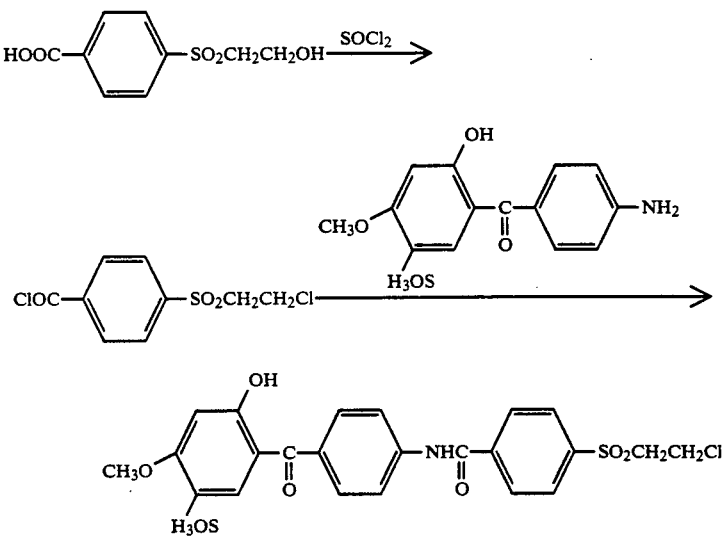

Proceeding in a manner similar to that described in Example III above, except replacing 4-(hydroxyethylsulfonylmethyl) benzoic acid with 4-(2-hydroxyethylsulfonyl) benzoic acid, there was obtained 4'-[4"-(2-chloroethylsulfonylphenyl) amino]-2-hydroxy-4-methoxybenzophenone-5-sulfonic acid as a pale yellow solid. A lens treated with this compound was found to be clear with good UV blockage up to about 360 nm.

What is claimed is:

1. An ultraviolet radiation absorbing lens comprising an effective amount of an ultraviolet absorbing agent bonded to a lens comprised of hydroxyethyl methacrylate polymer, wherein said agent comprises the formula:

A—NH—B wherein A is an ultraviolet radiation absorbing component and wherein B is a reactive group or a moiety containing reactive group selected from the group consisting of —SO$_2$CH$_2$CH$_2$—X; —SO$_2$CH$_2$CH$_2$—OSO$_3$Na;

—SO$_2$NHCH$_2$CH$_2$OSO$_3$Na;

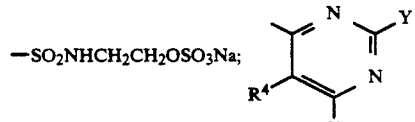

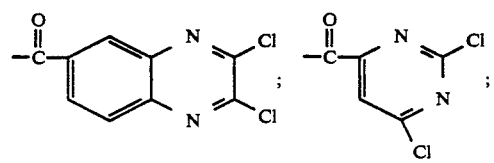

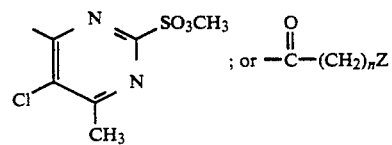

wherein
X = a halogen;
R$^4$ = H or Cl;
Y = Cl or F;
n = 1 or 2 and
Z = a halogen,

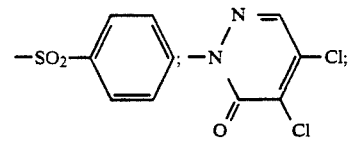

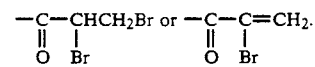

2. A method of preparing an ultraviolet absorbing lens, comprising the steps of contacting a lens comprising hydroxyethyl methacrylate polymer with a solution containing an effective amount of an ultraviolet radiation absorbing agent comprising the formula:

A—NH—B wherein A is an ultraviolet radiation absorbing component and wherein B is a reactive group or a moiety containing reactive group selected from the group consisting of —SO$_2$CH$_2$CH$_2$—X; —SO$_2$CH$_2$CH$_2$—OSO$_3$Na;

—SO$_2$NHCH$_2$CH$_2$OSO$_3$Na;

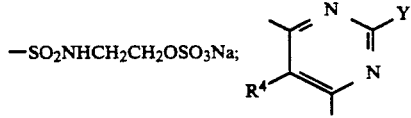

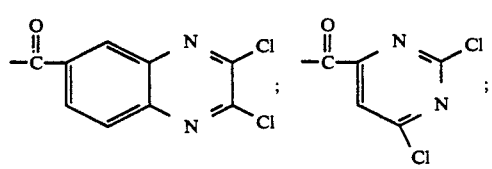

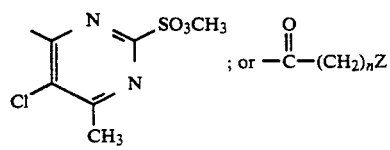

wherein
X = a halogen;
R$^4$ = H or Cl;
Y = Cl or F;
n = 1 or 2 and
Z = a halogen,

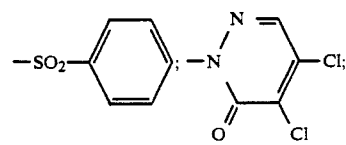

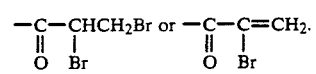

* * * * *